United States Patent
Zia et al.

(10) Patent No.: US 10,196,577 B2
(45) Date of Patent: Feb. 5, 2019

(54) LOW FRICTION SQUEAK FREE ASSEMBLY

(71) Applicant: Celanese Sales Germany GmbH, Sulzbach, Taunus (DE)

(72) Inventors: Qamer Zia, Frankfurt (DE); Peter Raab, Eppstein (DE); Kirsten Markgraf, Weinheim (DE)

(73) Assignee: Celanese Sales Germany GmbH, Sulzbach (Taunus) (DE)

( * ) Notice: Subject to any disclaimer, the term of this patent is extended or adjusted under 35 U.S.C. 154(b) by 0 days.

(21) Appl. No.: 15/282,062

(22) Filed: Sep. 30, 2016

(65) Prior Publication Data

US 2017/0088787 A1 Mar. 30, 2017

Related U.S. Application Data

(60) Provisional application No. 62/235,064, filed on Sep. 30, 2015.

(51) Int. Cl.
  *C10M 107/50* (2006.01)
  *C08L 59/02* (2006.01)
  (Continued)

(52) U.S. Cl.
  CPC ........ *C10M 107/50* (2013.01); *A47J 31/4403* (2013.01); *C08L 59/02* (2013.01); *C08L 59/04* (2013.01); *C10M 169/041* (2013.01); *F16C 29/02* (2013.01); *F16C 33/201* (2013.01); *A61M 5/31513* (2013.01); *A61M 15/009* (2013.01);
  (Continued)

(58) Field of Classification Search
  CPC .............................. C10M 107/50; C08L 59/02
  See application file for complete search history.

(56) References Cited

U.S. PATENT DOCUMENTS

| 3,574,786 A | 4/1971 | Ishida et al. |
|---|---|---|
| 3,629,310 A | 12/1971 | Bailey et al. |

(Continued)

FOREIGN PATENT DOCUMENTS

| CN | 101130621 | 2/2008 |
|---|---|---|
| CN | 101240092 | 8/2008 |

(Continued)

OTHER PUBLICATIONS

Kawaguchi et al., "Tensile Behavior of Glass-Fiber Filled Polyacetal: Influence of the Functional Groups of Polymer Matrices", Journal of Applied Polymer Science, Wiley, US, vol. 107, No. 1., Jan. 5, 2008, pp. 667-673.

(Continued)

*Primary Examiner* — Ellen M McAvoy
(74) *Attorney, Agent, or Firm* — Dority & Manning, P.A.

(57) ABSTRACT

A tribologically modified polyoxymethylene polymer composition is disclosed. The polyoxymethylene polymer composition is comprised of a polyoxymethylene polymer and at least one tribological modifier. The tribological modifier may comprise an ultra-high molecular weight silicone having a kinematic viscosity of greater than 100,000 $mm^2\ s^{-1}$. When tested against itself, the composition of the present disclosure exhibits an extremely low dynamic coefficient of friction and produces no discernible noise over a very broad temperature range, such as from −20° C. to 60° C.

13 Claims, 2 Drawing Sheets

(51) Int. Cl.
*A47J 31/44* (2006.01)
*C10M 169/04* (2006.01)
*C08L 59/04* (2006.01)
*F16C 33/20* (2006.01)
*F16C 29/02* (2006.01)
*A61M 5/315* (2006.01)
*A61M 15/00* (2006.01)
*A61M 5/31* (2006.01)

(52) U.S. Cl.
CPC ............... *A61M 2005/3131* (2013.01); *A61M 2205/0222* (2013.01); *C08L 2203/02* (2013.01); *C10M 2229/025* (2013.01); *C10N 2240/66* (2013.01); *C10N 2250/18* (2013.01); *F16C 2208/66* (2013.01); *F16C 2240/06* (2013.01); *F16C 2240/26* (2013.01)

(56) References Cited

U.S. PATENT DOCUMENTS

| | | |
|---|---|---|
| 4,111,887 A | 9/1978 | Shaner et al. |
| 4,161,470 A | 7/1979 | Calundann |
| 4,394,468 A | 7/1983 | Lu |
| 4,436,200 A | 3/1984 | Hodlewsky et al. |
| 4,455,273 A | 6/1984 | Harpell et al. |
| 4,480,071 A | 10/1984 | Natarajan |
| 4,493,751 A | 1/1985 | Cherdron et al. |
| 4,528,390 A | 7/1985 | Kimura |
| 4,645,785 A | 2/1987 | Heinz et al. |
| 4,652,594 A | 3/1987 | Auerbach et al. |
| 4,703,075 A | 10/1987 | Egami |
| 4,828,755 A | 5/1989 | Kusumgar et al. |
| 4,874,807 A | 10/1989 | Endo et al. |
| 4,879,331 A | 11/1989 | Endo et al. |
| 4,959,404 A | 9/1990 | Nakane et al. |
| 4,987,176 A | 1/1991 | Goerrissen et al. |
| 5,063,263 A | 11/1991 | Hayes et al. |
| 5,079,287 A | 1/1992 | Takeshi et al. |
| 5,177,123 A | 1/1993 | Takayama et al. |
| 5,212,222 A | 5/1993 | Mitsuuchi et al. |
| 5,237,008 A | 8/1993 | Kosinski |
| 5,264,516 A | 11/1993 | Hijikata et al. |
| 5,298,537 A | 3/1994 | Vaidya |
| 5,309,705 A | 5/1994 | Takahashi et al. |
| 5,310,822 A | 5/1994 | Kielhorn-Bayer et al. |
| 5,314,912 A | 5/1994 | Yoshitani et al. |
| 5,326,846 A | 7/1994 | Nagai et al. |
| 5,344,882 A | 9/1994 | Flexman |
| 5,346,737 A | 9/1994 | Takahashi et al. |
| 5,374,485 A | 12/1994 | Wakatsuka et al. |
| 5,415,791 A | 5/1995 | Chou et al. |
| 5,444,145 A | 8/1995 | Brant et al. |
| 5,482,987 A | 1/1996 | Forschirm |
| 5,530,061 A | 6/1996 | Sanada et al. |
| 5,538,793 A | 7/1996 | Inokuchi et al. |
| 5,559,180 A | 9/1996 | Takahashi et al. |
| 5,587,440 A | 12/1996 | Ehlers et al. |
| 5,616,680 A | 4/1997 | Linstid, III |
| 5,641,824 A | 6/1997 | Forschirm |
| 5,759,642 A | 6/1998 | Berger |
| 5,824,742 A | 10/1998 | Shinohara |
| 5,834,056 A | 11/1998 | Lutz |
| 5,852,135 A | 12/1998 | Kanai et al. |
| 5,854,324 A | 12/1998 | Tajima et al. |
| 5,886,066 A | 3/1999 | Forschirm |
| 5,889,102 A | 3/1999 | Haack et al. |
| 5,942,568 A | 8/1999 | Niino et al. |
| 5,977,229 A | 11/1999 | Barth et al. |
| 5,977,299 A | 11/1999 | Annunziato et al. |
| 6,013,723 A | 1/2000 | Akao |
| 6,046,141 A | 4/2000 | Kurz et al. |
| 6,077,908 A | 6/2000 | Yahiro |
| 6,080,486 A | 6/2000 | Falcone et al. |
| 6,114,492 A | 9/2000 | Linstid, III et al. |
| 6,130,280 A | 10/2000 | Yokoyama et al. |
| 6,161,685 A | 12/2000 | Stebnicki |
| 6,191,222 B1 | 2/2001 | Keller et al. |
| 6,207,769 B1 | 3/2001 | Gerlach et al. |
| 6,221,946 B1 | 4/2001 | Niino et al. |
| 6,238,733 B1 | 5/2001 | Therolf |
| 6,284,828 B1 | 9/2001 | Takayama |
| 6,360,881 B2 | 3/2002 | Stebnicki et al. |
| 6,384,179 B2 | 5/2002 | Tanimura et al. |
| 6,388,049 B1 | 5/2002 | Yokoyama et al. |
| 6,485,794 B1 | 11/2002 | Li et al. |
| 6,486,270 B1 | 11/2002 | Garrison et al. |
| 6,489,388 B1 | 12/2002 | Kurz |
| 6,506,850 B1 | 1/2003 | Tanimura et al. |
| 6,514,611 B1 | 2/2003 | Shepherd et al. |
| 6,545,081 B1 | 4/2003 | Nishihata et al. |
| 6,559,249 B2 | 5/2003 | Yang et al. |
| 6,586,501 B1 | 7/2003 | Dalton et al. |
| 6,590,032 B2 | 7/2003 | Furukawa et al. |
| 6,602,953 B1 | 8/2003 | Horio et al. |
| 6,616,918 B2 | 9/2003 | Candau |
| 6,664,313 B2 | 12/2003 | Hirai et al. |
| 6,737,475 B1 | 5/2004 | Tajima et al. |
| 6,753,363 B1 | 6/2004 | Harashina |
| 6,790,385 B2 | 9/2004 | Schleith et al. |
| 6,821,630 B2 | 11/2004 | Takada et al. |
| 6,852,677 B2 | 2/2005 | Kurz et al. |
| 7,056,965 B2 | 6/2006 | Seyama et al. |
| 7,067,182 B2 | 6/2006 | Li et al. |
| 7,183,340 B2 | 2/2007 | Harashina et al. |
| 7,186,766 B2 | 3/2007 | Harashina |
| 7,247,665 B1 | 7/2007 | Woerner |
| 7,256,966 B2 | 8/2007 | Horio et al. |
| 7,268,190 B2 | 9/2007 | Ohme et al. |
| 7,309,727 B2 | 12/2007 | Elkovitch et al. |
| 7,396,492 B2 | 7/2008 | Price |
| 7,488,539 B2 | 2/2009 | Kozakai et al. |
| 7,550,541 B2 | 6/2009 | Ohme et al. |
| 7,638,565 B2 | 12/2009 | Harashina |
| 7,645,821 B2 | 1/2010 | Disch et al. |
| 7,821,740 B2 | 10/2010 | Horio et al. |
| 7,851,585 B2 | 12/2010 | Brison et al. |
| 7,893,140 B2 | 2/2011 | Hase |
| 8,007,916 B2 | 8/2011 | Kuhmann et al. |
| 8,097,670 B2 | 1/2012 | Nagai et al. |
| 8,101,042 B2 | 1/2012 | Gantner et al. |
| 8,222,321 B2 | 7/2012 | Youm et al. |
| 8,324,296 B2 | 12/2012 | Kaneda et al. |
| 8,426,519 B2 | 4/2013 | Cogen et al. |
| 8,530,617 B2 | 9/2013 | Harimoto |
| 8,541,515 B1 | 9/2013 | Berg |
| 8,623,801 B2 | 1/2014 | Oki et al. |
| 8,829,085 B2 | 9/2014 | Markgraf et al. |
| 8,865,805 B2 | 10/2014 | Markgraf et al. |
| 9,062,183 B2 | 6/2015 | Markgraf |
| 9,187,634 B2 | 11/2015 | Sivebaek |
| 9,303,145 B2* | 4/2016 | Markgraf ............... C08G 18/56 |
| 9,422,428 B2 | 8/2016 | Kaushik et al. |
| 9,534,112 B2* | 1/2017 | Matoishi ................. C08L 23/26 |
| 9,540,553 B2 | 1/2017 | Markgraf |
| 9,567,460 B2 | 2/2017 | Lu |
| 9,676,935 B2* | 6/2017 | Hwang ................... C08L 59/02 |
| 10,030,208 B2* | 7/2018 | Zia ....................... C10M 155/02 |
| 2002/0040113 A1 | 4/2002 | Fritzsche et al. |
| 2003/0039834 A1* | 2/2003 | Gunn ....................... D01F 1/10 |
| | | 428/375 |
| 2003/0195280 A1 | 10/2003 | Disch et al. |
| 2004/0135118 A1 | 7/2004 | Waggoner |
| 2004/0155381 A1 | 8/2004 | Clark et al. |
| 2004/0158005 A1 | 8/2004 | Bloom |
| 2005/0004326 A1 | 1/2005 | Seargeant |
| 2005/0043492 A1 | 2/2005 | Chin et al. |
| 2005/0107513 A1 | 5/2005 | Papke |
| 2005/0167071 A1 | 8/2005 | Kendall et al. |
| 2006/0025507 A1 | 2/2006 | Moore et al. |
| 2006/0066746 A1 | 3/2006 | Lee et al. |
| 2007/0032605 A1 | 2/2007 | Harashina |
| 2007/0066746 A1 | 3/2007 | Gunnewig et al. |
| 2007/0082998 A1 | 4/2007 | Uosaki et al. |

(56) References Cited

U.S. PATENT DOCUMENTS

| | | | |
|---|---|---|---|
| 2007/0100055 A1 | 5/2007 | Uosaki et al. | |
| 2007/0100056 A1 | 5/2007 | Uosaki et al. | |
| 2007/0202332 A1 | 8/2007 | Gunnewig | |
| 2008/0234413 A1 | 9/2008 | Shinohara et al. | |
| 2009/0166911 A1 | 7/2009 | Uosaki et al. | |
| 2009/0177150 A1 | 7/2009 | Sivebaek | |
| 2009/0283931 A1 | 11/2009 | Pfeiffer et al. | |
| 2010/0022691 A1 | 1/2010 | Katsuchi et al. | |
| 2010/0093901 A1 | 4/2010 | Kawaguchi et al. | |
| 2011/0288226 A1 | 11/2011 | Mehta et al. | |
| 2012/0129976 A1* | 5/2012 | Ratnagiri | C08J 3/005 523/400 |
| 2012/0276314 A1 | 11/2012 | Latz et al. | |
| 2013/0047862 A1 | 2/2013 | Turi et al. | |
| 2013/0065993 A1 | 3/2013 | Backer et al. | |
| 2013/0066022 A1 | 3/2013 | Robert et al. | |
| 2013/0071663 A1 | 3/2013 | Ludtke et al. | |
| 2013/0079483 A1 | 3/2013 | Robert et al. | |
| 2013/0090400 A1 | 4/2013 | Robert et al. | |
| 2013/0180588 A1 | 7/2013 | Hufen et al. | |
| 2013/0241088 A1 | 9/2013 | Onai | |
| 2013/0331488 A1 | 12/2013 | Markgraf et al. | |
| 2014/0080951 A1 | 3/2014 | Raman | |
| 2014/0158947 A1 | 6/2014 | Oki et al. | |
| 2014/0316041 A1 | 10/2014 | Mehta | |
| 2015/0065654 A1* | 3/2015 | Markgraf | C08L 59/00 525/154 |
| 2015/0111794 A1 | 4/2015 | Zia et al. | |
| 2015/0111796 A1 | 4/2015 | Zia et al. | |
| 2015/0175787 A1* | 6/2015 | Zia | C08L 23/06 525/106 |
| 2015/0175928 A1 | 6/2015 | Zia et al. | |
| 2015/0274930 A1 | 10/2015 | Jon | |
| 2016/0177219 A1* | 6/2016 | Markgraf | C08K 7/14 508/107 |

FOREIGN PATENT DOCUMENTS

| | | |
|---|---|---|
| CN | 200810030809 | 8/2008 |
| CN | 101333316 | 12/2008 |
| CN | 200810031849 | 12/2008 |
| CN | 101343396 | 1/2009 |
| CN | 200910033254 | 6/2009 |
| CN | 101575429 | 11/2009 |
| CN | 101696292 | 4/2010 |
| CN | 200910035581 | 4/2010 |
| CN | 101759955 | 6/2010 |
| CN | 102898825 | 1/2013 |
| CN | 103788462 | 5/2014 |
| CN | 201410068870 | 5/2014 |
| DE | 2162345 | 7/1972 |
| DE | 4311634 | 10/1993 |
| DE | 102004057190 | 6/2006 |
| DE | 102008055840 | 5/2010 |
| EP | 0290230 | 9/1988 |
| EP | 0613923 | 9/1994 |
| EP | 1630198 A1 | 1/2006 |
| EP | 2532905 | 12/2012 |
| EP | 2653497 | 10/2013 |
| GB | 1331829 | 9/1973 |
| JP | S 5472300 | 6/1979 |
| JP | 55-145529 | 11/1980 |
| JP | 56-105905 | 8/1981 |
| JP | H 01126359 | 5/1989 |
| JP | H 01204950 | 8/1989 |
| JP | 3284675 | 12/1991 |
| JP | H 0488023 | 3/1992 |
| JP | H 04-234450 | 8/1992 |
| JP | H 05295230 | 11/1993 |
| JP | H05-320435 | 12/1993 |
| JP | 06-099470 | 4/1994 |
| JP | 1992253121 | 4/1994 |
| JP | H06-033334 | 5/1994 |
| JP | 6179671 | 6/1994 |
| JP | 7010871 | 1/1995 |
| JP | 7033766 | 2/1995 |
| JP | H 0867798 | 3/1996 |
| JP | H 08-311351 | 11/1996 |
| JP | H 11 181232 | 7/1999 |
| JP | H 11181231 | 7/1999 |
| JP | 2000109702 | 4/2000 |
| JP | 2000154181 | 6/2000 |
| JP | 3081610 | 8/2000 |
| JP | 2000-336241 | 12/2000 |
| JP | 1992158616 | 1/2002 |
| JP | 4741120 | 6/2002 |
| JP | 2003026851 | 1/2003 |
| JP | 2005-289610 | 10/2005 |
| JP | 2005-289611 | 10/2005 |
| JP | 2004110244 A | 10/2005 |
| JP | 2004110245 A | 10/2005 |
| JP | 2008-156561 | 7/2008 |
| JP | 2006349668 | 7/2008 |
| JP | 2009-286874 | 12/2009 |
| JP | 2010037445 | 2/2010 |
| JP | 2010-110159 | 5/2010 |
| JP | 2008281362 | 5/2010 |
| JP | 2010-202800 | 9/2010 |
| JP | 200950985 | 9/2010 |
| JP | 2011246566 | 12/2011 |
| KR | 100915000 | 9/2009 |
| TW | 201033277 | 9/2010 |
| WO | WO 99/46331 | 9/1999 |
| WO | WO 2005/059030 | 6/2005 |
| WO | WO 2006/042571 | 4/2006 |
| WO | WO 2006/105918 A1 | 12/2006 |
| WO | WO 2010/035351 A1 | 1/2010 |
| WO | WO PCT/ JP2009/066892 | 4/2010 |
| WO | WO 2010/073529 | 7/2010 |

OTHER PUBLICATIONS

Zhang et al., Study on Property and Structure of Glass-Fiber-Reinforced Polyoxymethylene Composites; The Center of Research and Development, Jushi Group Col, Ltd. Tongxiang, Peoples Republic of China 2009; 37(4), 6-9.

GUR® PE-UHMW, Ticona Product Info, 38 pages.

www.canplastics.com/features/additive-improves-acetal-processing/; Canadian Plastics, Additive Improves Acetal Processing, dated Jul. 1, 1999, 5 pages.

Polytetrafluoroethylene Filled Ultra-High Molecular Weight Polyethylene Composite: Mechanical and Wear Property Relationships, Silverstein et al., Polymer Engineering and Science, Nov. 1995, vol. 35, No. 22, pp. 1785-1794.

Laursen J L et al; "Influence of tribological additives on friction and impact performance of injection moulded polyacetal", Wear, Elsevier Sequoia, Lausanne, CH, vol. 267, No. 12, Dec. 1, 2009, pp. 2294-2302, XP026751088.

Japanese Abstract of JPH03244636 dated Oct. 31, 1991, 2 pages.

GUR® PE-UHMW, Ticona Product Info, 4 pages.

Silicone Powder, Shin-Etsu, 2004.

Dow Coming® Si Powder Resin Modifiers, Production Information, 2011.

PCT/IB2016/055884 International Search Report and Written Opinion, dated Jan. 25, 2017, 12 pages.

Mas Rusplast, Our solutions. Polyacetal Kepital: wear-resistant friction units, machine translation, Sep. 6, 2011, 1 page.

Tekuma Kunststoff GMBH, Kepital TS-25H data sheet, 1 page, www.tekuma.de.

Abstract only CN104693696, Jun. 10, 2015, 1 page.

Abstract only CN102585433, Jul. 18, 2012, 2 pages.

Abstract only DE102008055840, May 12, 2010, 1 page.

\* cited by examiner

LOW FRICTION SQUEAK FREE ASSEMBLY

RELATED APPLICATIONS

The present application is based upon and claims priority to U.S. provisional Application having Ser. No. 62/235,064, filed on Sep. 30, 2015 and which is incorporated herein by reference.

BACKGROUND

Polyacetal polymers, which are commonly referred to as polyoxymethylene polymers, have become established as exceptionally useful engineering materials in a variety of applications. For instance, because polyoxymethylene polymers have excellent mechanical properties, fatigue resistance, abrasion resistance, chemical resistance, and moldability, they are widely used in constructing polymer articles, such as articles for use in the automotive industry and the electrical industry.

The mechanical properties of polyoxymethylene molding compositions are one of the reasons for their use in numerous applications. To improve their properties, polyoxymethylene polymers are often provided with additives to adapt the properties for a specific application, for example by using reinforcing fibers or tribological modifiers. For instance, polyoxymethylene polymers have been combined with a tribological modifier for producing polymer compositions well suited for use in tribological applications where the polymer article is in moving contact with other articles, such as metal articles, plastic articles, and the like. These tribological applications can include embodiments where the polymer composition is formed into gear wheels, pulleys, sliding elements, and the like. The addition of a tribological modifier can provide a composition with a reduced coefficient of friction, low frictional noise, and low wear.

In the past, high molecular weight polyolefins have been used to improve the wear resistance of polyoxymethylene resins. For instance, U.S. Pat. No. 5,482,987, which is incorporated herein by reference in its entirety, discloses a self-lubricating, low wear composition containing a polyoxymethylene and a lubricating system comprising a high molecular weight polyethylene, a high density polyethylene, and other components. U.S. Pat. No. 5,641,824, which is incorporated herein by reference in its entirety, discloses a self-lubricating melt blend of a polyoxymethylene and an ultra-high molecular weight polyethylene. A tribologically modified polyoxymethylene polymer composition is also disclosed in U.S. Patent Publication No. 2015/0111796, which is also incorporated herein by reference.

Although polyoxymethylene polymers have been tribologically modified in the past, further improvements are still necessary. For instance, many tribological modifiers for polyoxymethylene polymers are temperature sensitive. Many tribological modifiers either do not work at high temperature or at low temperature. Consequently, a need exists for a tribological modifier for polyoxymethylene polymers that can operate over an extended range of temperatures.

In addition, in many applications, a component made from a thermoplastic polymer is intended to slide against, rub against, or otherwise contact during movement another component also made from a thermoplastic polymer. It is desirable in certain applications for the two components to contact each other without creating noise associated with the stick-slip phenomenon. Noise generation, for instance, is particularly problematic in consumer appliances and other consumer products where noise generation is highly undesirable. Noise generation in these applications is also influenced by the application temperature. Thus, a need also exists for a tribological modifier that can be incorporated into a polyoxymethylene polymer that not only has functionality over a wide temperature range but can also lead to decreased noise generation when contacting another component.

SUMMARY

The present disclosure is generally directed to a polymer composition containing a thermoplastic polymer and a tribological modifier and to shaped articles made from the polymer composition. In accordance with the present disclosure, the tribological modifier incorporated into the composition is capable of reducing the friction properties of the polymer even over an extended temperature range. Of particular advantage, parts and articles made in accordance with the present disclosure have characteristics and properties that make the parts and articles well suited for use in applications where the product or article slides against an opposing surface. Even over a very large temperature range, for instance, the articles and products produce no audible noise when sliding against an opposing component or part, especially when the opposing component or part is also made from the same or a similar polymer composition.

In one embodiment, the present disclosure is directed to a low friction assembly comprising a first sliding member in operative association with a second sliding member. The first sliding member and the second sliding member are configured to remain in contact and move relative to each other. Each sliding member comprises a molded polymeric article. The first sliding member is made from a first polymer composition comprising a polyoxymethylene polymer combined with an ultrahigh molecular weight silicone. The second sliding member is made from a second polymer composition also containing a polyoxymethylene polymer combined with an ultrahigh molecular weight silicone. The ultrahigh molecular weight silicone can be present in the first polymer composition and the second polymer composition such that when the polymer compositions are tested against each other, the compositions exhibit a dynamic coefficient of friction of less than about 0.06, even when tested at relatively high temperatures, such as at a temperature of 60° C. and at a sliding speed of 8 mm/s. In addition, the first sliding member can exhibit a wear track width of less than 0.5 mm when tested against a countermaterial at 60° C. at a force of 30 N and at a velocity of 8 mm/s after 1,000 cycles. The countermaterial can comprise the polyoxymethylene polymer contained in the sliding member. The second sliding member can also exhibit similar wear track characteristics.

The polyoxymethylene polymer contained in the first sliding member and the polyoxymethylene polymer contained in the second sliding member can be the same or can be different. In addition, the ultrahigh molecular weight silicone contained in the first sliding member can be the same or a different from the silicone contained in the second sliding member. The first polymer composition and the second polymer composition can contain the ultrahigh molecular weight silicone in the same amounts or in different amounts. In one embodiment, the ultrahigh molecular weight silicone is contained in the first polymer composition and the second polymer composition in an amount from about 0.5% to about 10% by weight, such as in an amount from about 0.5% to about 8% by weight, such as in an amount from about 1% to about 5% by weight. The ultrahigh molecular weight silicone can have a kinematic viscosity of greater than about 100,000 mm$^2$ s$^{-1}$. The ultrahigh molecular weight silicone, in one embodiment, can be an ultrahigh molecular weight polydimethylsiloxane. In one embodiment, the first sliding member and the second sliding member are both free of any silicone oils.

The first sliding member may comprise, for instance, a gear, a lever, a cam, a roller, a pulley, a latch, or a claw.

In one embodiment, the low friction assembly is contained in an apparatus. The apparatus can have an operating environment of greater than 25° C., such as greater than about 40° C., such as greater than about 50° C., such as greater than about 60° C. The operating environment can comprise an internal environment within the apparatus or can comprise an external environment. The internal environment, for instance, may have a high temperature due to heat being generated by the apparatus. Alternatively, the operating environment may comprise an external environment in which the apparatus operates. In one embodiment, the environment of the apparatus may also include temperatures less than 0° C. The apparatus, for instance, may comprise an automotive subassembly, a household appliance, or a conveyor system. In one particular embodiment, the apparatus comprises a coffeemaker.

Other features and aspects of the present disclosure are discussed in greater detail below.

BRIEF DESCRIPTION OF DRAWINGS

A full and enabling disclosure of the present disclosure is set forth more particularly in the remainder of the specification, including reference to the accompanying figures in which.

DETAILED DESCRIPTION

Figure 1:
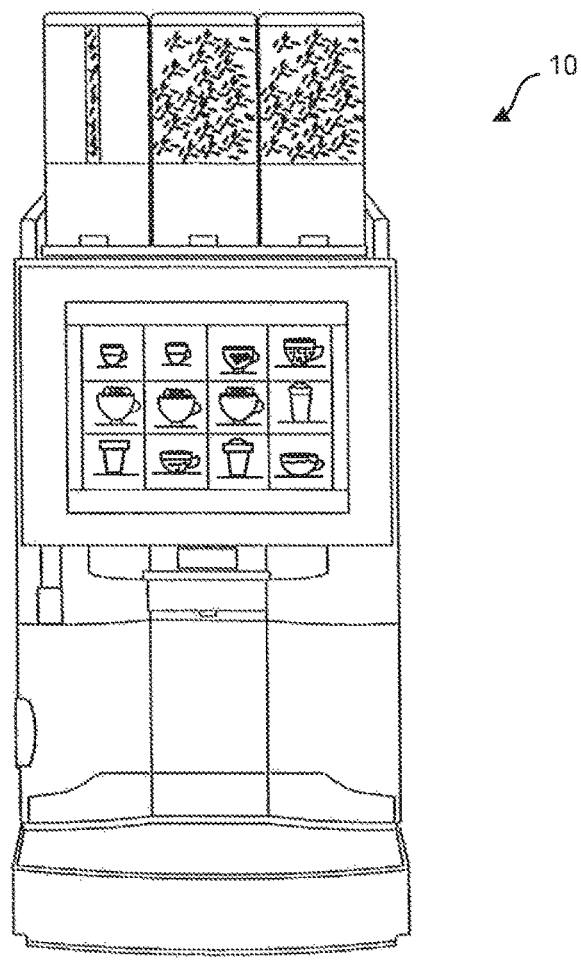
FIG. 1 is a perspective view of a coffee maker apparatus in accordance with the present disclosure.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations.

In general, the present disclosure is directed to a polyoxymethylene polymer composition and a polymer article comprising the polyoxymethylene polymer composition with improved tribological properties such as a reduced coefficient of friction. The tribological properties are improved by utilizing a tribological modifier. In general, the polyoxymethylene polymer composition comprises a polyoxymethylene polymer and an ultra-high molecular weight silicone.

The stick-slip phenomenon refers to the manner in which two opposing surfaces or articles slide over each other in reaction to the forces of friction. Static friction refers to the friction between two or more objects that are not moving relative to each other. Kinetic friction, on the other hand, occurs when two objects are moving relative to each other while remaining in contact. In order for one object to slide relative to another object, enough force must be exerted on one object to overcome the forces of static friction. When movement between the two objects occurs, a reduction of the friction between the two surfaces can cause a sudden increase in the velocity of movement. In other words, once one object moves relative to another object, in some applications, less force is needed to continue movement. The friction between the two surfaces can increase or decrease during movement depending upon numerous factors, including the speed at which movement continues. Stick-slip describes how surfaces alternate between sticking to each other and sliding over each other as movement occurs between two surfaces and as the conditions of movement change.

As two surfaces move relative to each other and the stick-slip phenomenon occurs, noise can be generated from the two surfaces. Depending upon the stick-slip properties of the materials, noise generation can be highly audible or very quiet. The amount of noise generation occurring during the stick-slip phenomenon may not only depend upon the material from which the surfaces are made, but can also depend upon the temperature of the environment. In many applications, the generation of noise caused by the stick-slip phenomenon when two components are sliding against each other is highly undesirable. For instance, when designing and manufacturing consumer products including consumer appliances, motor vehicles, household products and the like, manufacturers and engineers try to design products so that no noise generation occurs when the products are in use. Noise generation during use of the product, for instance, can create an impression with the consumer that the product is of inferior quality and made with inexpensive materials.

The present disclosure is particularly directed to a polymer composition that can be used to make molded parts such that when the parts slide against each other noise generation is inhibited and even eliminated. Of particular advantage, compositions made according to the present disclosure can be used to create opposing sliding members that have reduced friction characteristics over an extremely broad temperature range which thus prevents the sliding members from generating noise over the entire operating temperatures of the product.

For example, in one embodiment, the present disclosure is directed to a low friction assembly that includes a first sliding member in operative association with a second sliding member. The first sliding member and the second sliding member can both be made from a polymer composition formulated in accordance with the present disclosure. For instance, each sliding member can be made from a polymer composition containing a polyoxymethylene polymer combined with an ultrahigh molecular weight silicone. When tested against each other, the composition can be formulated so as to exhibit a dynamic coefficient of friction of less than about 0.07, such as less than about 0.06, such as less than about 0.05, such as less than about 0.04, such as even less than about 0.03 when tested at any temperature within the range of from about −20° C. to 60° C., such as from about 0° C. to about 60° C. The compositions or molded parts can be tested against each other according to a stick-slip test having Test No. VDA 230-206.

Specimens tested using the above method can also be analyzed to measure a wear track width which is an abrasion width. In accordance with the present disclosure, the compositions and molded articles can exhibit a wear track width of less than 0.5 mm, such as less than about 0.45 mm, such as even less than about 0.4 mm when tested at a force of 30 N and at a velocity of 8 mm/s after 1,000 cycles. Compositions made in accordance with the present disclosure can possess the above wear track characteristics at a temperature of anywhere between −20° C. and 60° C., such as from about 0° C. to about 60° C.

Compositions and sliding members made in accordance with the present disclosure, as indicated above, have reduced friction characteristics and thus have low noise properties over a very broad temperature range. These results are particularly surprising and unexpected at higher temperatures. At higher temperatures, for instance, the effects of many tribological modifiers on the thermoplastic polymer have a tendency to degrade.

The sliding members of the present disclosure are generally made from a thermoplastic polymer and a tribological modifier. In one embodiment, the thermoplastic polymer comprises a polyoxymethylene polymer, while the tribological modifier comprises an ultrahigh molecular weight silicone. In one particular embodiment, the composition is free from lower molecular weight silicone, such as a silicone oil. Incorporating the tribological modifier into a composition containing the thermoplastic polymer results in a composition having improved sliding properties at a reduced coefficient of friction against other surfaces, and particularly against an opposing surface made from the same or a similar composition.

Polyoxymethylene Polymer

According to one embodiment, the thermoplastic polymer composition comprises a polyoxymethylene polymer.

The preparation of the polyoxymethylene polymer can be carried out by polymerization of polyoxymethylene-forming monomers, such as trioxane or a mixture of trioxane and a cyclic acetal such as dioxolane in the presence of ethylene glycol as a molecular weight regulator. The polyoxymethylene polymer used in the polymer composition may comprise a homopolymer or a copolymer. According to one embodiment, the polyoxymethylene is a homo- or copolymer which comprises at least 50 mol. %, such as at least 75 mol. %, such as at least 90 mol. % and such as even at least 97 mol. % of —CH$_2$O-repeat units.

In one embodiment, a polyoxymethylene copolymer is used. The copolymer can contain from about 0.1 mol. % to about 20 mol. % and in particular from about 0.5 mol. % to about 10 mol. % of repeat units that comprise a saturated or ethylenically unsaturated alkylene group having at least 2 carbon atoms, or a cycloalkylene group, which has sulfur atoms or oxygen atoms in the chain and may include one or more substituents selected from the group consisting of alkyl cycloalkyl, aryl, aralkyl, heteroaryl, halogen or alkoxy. In one embodiment, a cyclic ether or acetal is used that can be introduced into the copolymer via a ring-opening reaction.

Preferred cyclic ethers or acetals are those of the formula:

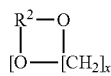

in which x is 0 or 1 and R$^2$ is a C$_2$-C$_4$-alkylene group which, if appropriate, has one or more substituents which are C$_1$-C$_4$-alkyl groups, or are C$_1$-C$_4$-alkoxy groups, and/or are halogen atoms, preferably chlorine atoms. Merely by way of example, mention may be made of ethylene oxide, propylene 1,2-oxide, butylene 1,2-oxide, butylene 1,3-oxide, 1,3-dioxane, 1,3-dioxolane, and 1,3-dioxepan as cyclic ethers, and also of linear oligo- or polyformals, such as polydioxolane or polydioxepan, as comonomers.

It is particularly advantageous to use copolymers composed of from 99.5 to 95 mol. % of trioxane and of from 0.5 to 5 mol. %, such as from 0.5 to 4 mol. %, of one of the above-mentioned comonomers.

The polymerization can be effected as precipitation polymerization or in the melt. By a suitable choice of the polymerization parameters, such as duration of polymerization or amount of molecular weight regulator, the molecular weight and hence the MVR value of the resulting polymer can be adjusted.

In one embodiment, a polyoxymethylene polymer with hydroxyl terminal groups can be produced using a cationic polymerization process followed by solution hydrolysis to remove any unstable end groups. During cationic polymerization, a glycol, such as ethylene glycol can be used as a chain terminating agent. The cationic polymerization results in a bimodal molecular weight distribution containing low molecular weight constituents. In one particular embodiment, the low molecular weight constituents can be significantly reduced by conducting the polymerization using a heteropoly acid such as phosphotungstic acid as the catalyst. When using a heteropoly acid as the catalyst, for instance, the amount of low molecular weight constituents can be less than about 2 wt. %.

A heteropoly acid refers to polyacids formed by the condensation of different kinds of oxo acids through dehydration and contains a mono- or poly-nuclear complex ion wherein a hetero element is present in the center and the oxo acid residues are condensed through oxygen atoms. Such a heteropoly acid is represented by the formula:

wherein

M represents an element selected from the group consisting of P, Si, Ge, Sn, As, Sb, U, Mn, Re, Cu, Ni, Ti, Co, Fe, Cr, Th or Ce, M' represents an element selected from the group consisting of W, Mo, V or Nb, m is 1 to 10, n is 6 to 40, z is 10 to 100, x is an integer of 1 or above, and y is 0 to 50.

The central element (M) in the formula described above may be composed of one or more kinds of elements selected from P and Si and the coordinate element (M') is composed of at least one element selected from W, Mo and V, particularly W or Mo.

Specific examples of heteropoly acids are phosphomolybdic acid, phosphotungstic acid, phosphomolybdotungstic acid, phosphomolybdovanadic acid, phosphomolybdotungstovanadic acid, phosphotungstovanadic acid, silicotungstic acid, silicomolybdic acid, silicomolybdotungstic acid, silicomolybdotungstovanadic acid and acid salts thereof. Excellent results have been achieved with heteropoly acids selected from 12-molybdophosphoric acid (H$_3$PMo$_{12}$O$_{40}$) and 12-tungstophosphoric acid (H$_3$PW$_{12}$O$_{40}$) and mixtures thereof.

The heteropoly acid may be dissolved in an alkyl ester of a polybasic carboxylic acid. It has been found that alkyl esters of polybasic carboxylic acid are effective to dissolve the heteropoly acids or salts thereof at room temperature (25° C.).

The alkyl ester of the polybasic carboxylic acid can easily be separated from the production stream since no azeotropic mixtures are formed. Additionally, the alkyl ester of the polybasic carboxylic acid used to dissolve the heteropoly acid or an acid salt thereof fulfills the safety aspects and environmental aspects and, moreover, is inert under the conditions for the manufacturing of oxymethylene polymers.

Preferably the alkyl ester of a polybasic carboxylic acid is an alkyl ester of an aliphatic dicarboxylic acid of the formula:

(ROOC)—(CH$_2$)n-(COOR')

wherein
n is an integer from 2 to 12, preferably 3 to 6 and
R and R' represent independently from each other an alkyl group having 1 to 4 carbon atoms, preferably selected from the group consisting of methyl, ethyl, n-propyl, iso-propyl, n-butyl, iso-butyl and tert.-butyl.

In one embodiment, the polybasic carboxylic acid comprises the dimethyl or diethyl ester of the above-mentioned formula, such as a dimethyl adipate (DMA).

The alkyl ester of the polybasic carboxylic acid may also be represented by the following formula:

(ROOC)$_2$—CH—(CH$_2$)m-CH—(COOR')$_2$ wherein
m is an integer from 0 to 10, preferably from 2 to 4 and
R and R' are independently from each other alkyl groups having 1 to 4 carbon atoms, preferably selected from the group consisting of methyl, ethyl, n-propyl, iso-propyl, n-butyl, iso-butyl and tert.-butyl.

Particularly preferred components which can be used to dissolve the heteropoly acid according to the above formula are butantetracarboxylic acid tetratethyl ester or butantetracarboxylic acid tetramethyl ester.

Specific examples of the alkyl ester of a polybasic carboxylic acid are dimethyl glutaric acid, dimethyl adipic acid, dimethyl pimelic acid, dimethyl suberic acid, diethyl glutaric acid, diethyl adipic acid, diethyl pimelic acid, diethyl suberic acid, dimethyl phthalic acid, dimethyl isophthalic acid, dimethyl terephthalic acid, diethyl phthalic acid, diethyl isophthalic acid, diethyl terephthalic acid, butantetracarboxylic acid tetramethylester and butantetracarboxylic acid tetraethylester as well as mixtures thereof. Other examples include dimethylisophthalate, diethylisophthalate, dimethyfterephthalate or diethylterephthalate.

Preferably, the heteropoly acid is dissolved in the alkyl ester of the polybasic carboxylic acid in an amount lower than 5 wt. %, preferably in an amount ranging from 0.01 to 5 wt. %, wherein the weight is based on the entire solution.

In some embodiments, the polymer composition of the present disclosure may contain other polyoxymethylene homopolymers and/or polyoxymethylene copolymers. Such polymers, for instance, are generally unbranched linear polymers which contain at least 80%, such as at least 90%, oxymethylene units, The polyoxymethylene polymer can have any suitable molecular weight. The molecular weight of the polymer, for instance, can be from about 4,000 grams per mole to about 20,000 g/mol. In other embodiments, however, the molecular weight can be well above 20,000 g/mol, such as from about 20,000 g/mol to about 100,000 g/mol.

The polyoxymethylene polymer present in the composition can generally melt flow index (MFI) ranging from about 1 to about 50 g/10 min, as determined according to ISO 1133 at 190° C. and 2.16 kg, though polyoxymethylenes having a higher or lower melt flow index are also encompassed herein. For example, the polyoxymethylene polymer may be a low or mid-molecular weight polyoxymethylene that has a melt flow index of greater than about 5 g/10 min, greater than about 10 g/10 min, or greater than about 15 g/10 min. The melt flow index of the polyoxymethylene polymer can be less than about 25 g/10 min, less than about 20 g/10 min, less than about 18 g/10 min, less than about 15 g/10 min, less than about 13 g/10 min, or less than about 12 g/10 min. The polyoxymethylene polymer may for instance be a high molecular weight polyoxymethylene that has a melt flow index of less than about 5 g/10 min, less than about 3 g/10 min, or less than about 2 g/10 min.

The polyoxymethylene polymer may contain a relatively high amount of functional groups, such as hydroxyl groups in the terminal positions. More particularly, the polyoxymethylene polymer can have terminal hydroxyl groups, for example hydroxyethylene groups and/or hydroxyl side groups, in at least more than about 50% of all the terminal sites on the polymer. It should be understood that the total number of terminal groups present includes all side terminal groups. In addition to the terminal hydroxyl groups, the polyoxymethylene polymer may also have other terminal groups usual for these polymers such as alkoxy groups, formate groups, acetate groups or hemiacetal groups. In one embodiment, the polyoxymethylene polymer can have a content of terminal hydroxyl groups of at least 5 mmol/kg, such as at least 10 mmol/kg, such as at least 15 mmol/kg. In one embodiment, for instance, the polymer may contain terminal hydroxyl groups in an amount greater than 17 mmol/kg, such as greater than about 18 mmol/kg, such as greater than about 19 mmol/kg, such as greater than 20 mmol/kg. The terminal hydroxyl group content is generally less than about 100 mmol/kg, such as less than about 50 mmol/kg.

The polyoxymethylene polymer may also optionally have a relatively low amount of low molecular weight constituents. As used herein, low molecular weight constituents (or fractions) refer to constituents having molecular weights below 10,000 dalton. In this regard, the polyoxymethylene polymer can contain low molecular weight constituents in an amount less than about 10 wt. %, based on the total weight of the polyoxymethylene. In certain embodiments, for instance, the polyoxymethylene polymer may contain low molecular weight constituents in an amount less than about 5 wt. %, such as in an amount less than about 3 wt. %, such as even in an amount less than about 2 wt. %.

Suitable commercially available polyoxymethylene polymers are available under the trade name Hostaform® (HF) by Celanese/Ticona.

The polyoxymethylene polymer may be present in the polyoxymethylene polymer composition in an amount of at least 60 wt. %, such as at least 70 wt. %, such as at least 80 wt. %, such as at least 85 wt. %, such as at least 90 wt. %, such as at least 95 wt. %. In general, the polyoxymethylene polymer is present in an amount of less than about 100 wt. %, such as less than about 99 wt. %, such as less than about 97 wt. %, wherein the weight is based on the total weight of the polyoxymethylene polymer composition.

Tribological Modifier.

According to the present disclosure, the polyoxymethylene polymer composition and the polymer article comprising the polyoxymethylene polymer composition may comprise at least one tribological modifier.

In one embodiment, ultra-high molecular weight silicone (UHMW-Si) may be used to modify the polyoxymethylene polymer. In general, the UHMW-Si can have an average molecular weight of greater than 100,000 g/mol, such as greater than about 200,000 g/mol, such as greater than about 300,000 g/mol, such as greater than about 500,000 g/mol and less than about 3,000,000 g/mol, such as less than about 2,000,000 g/mol, such as less than about 1,000,000 g/mol, such as less than about 500,000 g/mol, such as less than about 300,000 g/mol. Generally, the UHMW-Si can have a kinematic viscosity at 40° C. measured according to DIN 51562 of greater than 100,000 mm$^2$ s$^{-1}$, such as greater than about 200,000 mm$^2$ s$^{-1}$, such as greater than about 1,000,000 mm$^2$ s$^{-1}$, such as greater than about 5,000,000 mm$^2$ s$^{-1}$, such as greater than about 10,000,000 mm$^2$ s$^{-1}$, such as greater than about 15,000,000 mm$^2$ s$^{-1}$ and less than about 50,000,000 mm$^2$ s$^{-1}$, such as less than about 25,000,000 mm$^2$ s$^{-1}$, such as less than about 10,000,000 mm$^2$ s$^{-1}$, such as less than about 1,000,000 mm$^2$ s$^{-1}$, such as less than about 500,000 mm$^2$ s$^{-1}$, such as less than about 200,000 mm$^2$ s$^{-1}$.

The UHMW-Si may comprise a siloxane such as a polysiloxane or polyorganosiloxane. In one embodiment, the UHMW-Si may comprise a dialkylpolysiloxane such as a dimethylsiloxane, an alkylarylsiloxane such as a phenylmethylsiloxane, a polysilsesquioxane, or a diarylsiloxane such as a diphenylsiloxane, or a homopolymer thereof such as a polydimethylsiloxane or a polymethylphenylsiloxane, or a copolymer thereof with the above molecular weight and/or kinematic viscosity requirements. The polysiloxane or polyorganosiloxane may also be modified with a substituent such as an epoxy group, a hydroxyl group, a carboxyl group, an amino group or a substituted amino group, an ether group, or a meth(acryloyl) group in the end or main chain of the molecule. The UHMW-Si compounds may be used singly or in combination. Any of the above UHMW-Si compounds may be used with the above molecular weight and/or kinematic viscosity requirements.

The UHMW-Si may be added to the polyoxymethylene polymer composition as a masterbatch wherein the UHMW-Si is dispersed in a polyoxymethylene polymer and the masterbatch is thereafter added to another polyoxymethylene polymer. The masterbatch may comprise from about 10 wt. % to about 50 wt. %, such as from about 35 wt. % to about 45 wt. %, such as about 40 wt. % of an UHMW-Si.

The UHMW-Si may be present in the polyoxymethylene polymer composition in an amount of greater than about 0 wt. %, such as at greater than about 0.1 wt. %, such as at greater than about 0.5 wt. %, such as at greater than about 0.75 wt. %, such as at greater than about 1 wt. %, such as at greater than about 2 wt. %, such as at greater than about 2.5 wt. % and generally less than about 10 wt. %, such as less than about 6 wt. %, such as less than about 5 wt. %, such as less than about 4 wt. %, such as less than about 3.5 wt. %, such as less than about 3 wt. %, wherein the weight is based on the total weight of the polyoxymethylene polymer composition.

The present inventors discovered that ultrahigh molecular weight silicone, when combined with a polyoxymethylene polymer, dramatically reduced the coefficient of friction of the resulting composition over an extended temperature range, even at high temperatures such as at temperatures higher than 30° C., such as greater than 50° C., such as even greater than 60° C. Polyoxymethylene polymers combined with other known tribological modifiers, on the other hand, have a tendency to undergo an increase in the coefficient of friction, increase in system wear and audible noise generation, as temperatures increase. In one embodiment, the polymer composition of the present disclosure only contains a single tribological modifier, which comprises the ultrahigh molecular weight silicone. In other embodiments, however, the composition may contain other tribological modifiers in combination with the ultrahigh molecular weight silicone. Other tribological modifiers that may be present, for instance, include boron nitride, polytetrafluoroethylene particles, calcium carbonate particles, ultrahigh molecular weight polyethylene particles, stearyl stearate particles, and one or more waxes, such as polyethylene wax, an amide wax, wax particles comprising an aliphatic ester wax comprised of a fatty acid of a monohydric alcohol, a graft copolymer with olefin polymer as a graft base, mixtures thereof, and the like. The other tribological modifiers may be present in the composition in an amount from about 0.1% to about 5% by weight each, such as from about 0.1% to about 2% by weight.

In one embodiment, the composition is substantially free of lower molecular weight silicones, such as silicone oils. In one embodiment, for instance, the composition contains no silicones having a molecular weight of less than about 75,000 g/mol, such as less than about 50,000 g/mol, such as less than about 20,000 g/mol, such as less than about 5,000 g/mol.

Other Additives

The polymer composition of the present disclosure may also contain other known additives such as, for example, antioxidants, formaldehyde scavengers, acid scavengers, UV stabilizers or heat stabilizers, reinforcing fibers. In addition, the compositions can contain processing auxiliaries, for example adhesion promoters, lubricants, nucleants, demolding agents, fillers, colorants such as pigments or antistatic agents and additives which impart a desired property to the compositions and articles or parts produced therefrom.

In one embodiment, an ultraviolet light stabilizer may be present. The ultraviolet light stabilizer may comprise a benzophenone, a benzotriazole, or a benzoate. The UV light absorber, when present, may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a formaldehyde scavenger, such as a nitrogen-containing compound, may be present. Mainly, of these are heterocyclic compounds having at least one nitrogen atom as hetero atom which is either adjacent to an amino-substituted carbon atom or to a carbonyl group, for example pyridine, pyrimidine, pyrazine, pyrrolidone, aminopyridine and compounds derived therefrom. Other particularly advantageous compounds are triamino-1,3,5-triazine (melamine) and its derivatives, such as melamine-formaldehyde condensates and methylol melamine. Oligomeric polyamides are also suitable in principle for use as formaldehyde scavengers. The formaldehyde scavenger may be used individually or in combination.

Further, the formaldehyde scavenger may be a guanamine compound which may include an aliphatic guanamine-based compound, an alicyclic guanamine-based compound, an aromatic guanamine-based compound, a hetero atom-containing guanamine-based compound, or the like. The formaldehyde scavenger may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, an acid scavenger may be present. The acid scavenger may comprise, for instance, an alkaline earth metal salt. For instance, the acid scavenger may comprise a calcium salt, such as a calcium citrate. The acid scavenger may be present in an amount of at least about 0.001 wt. %, such as at least about 0.005 wt. %, such as at least about 0.0075 wt. % and less than about 1 wt. %, such as less than about 0.75 wt. %, such as less than about 0.5 wt. %, wherein the weight is based on the total weight of the respective polymer composition.

In one embodiment, a nucleant may be present. The nucleant may increase crystallinity and may comprise an oxymethylene terpolymer. In one particular embodiment, for instance, the nucleant may comprise a terpolymer of butanediol diglycidyl ether, ethylene oxide, and trioxane. The nucleant may be present in the composition in an amount of at least about 0.01 wt. %, such as at least about 0.05 wt. %, such as at least about 0.1 wt. % and less than about 2 wt. %, such as less than about 1.5 wt. %, such as less than about 1 wt. %, wherein the weight is based on the total weight of the respective polymer composition.

In one embodiment, an antioxidant, such as a sterically hindered phenol, may be present. Examples which are available commercially, are pentaerythrityl tetrakis[3-(3,5-di-tert-butyl-4-hydroxyphenyl)propionate], triethylene glycol bis[3-(3-tert-butyl-4-hydroxy-5-methylphenyl)propionate], 3,3'-bis[3-(3,5-di-tert-butyl-4-hydroxyphenyl) propionohydrazide], and hexamethylene glycol bis[3-(3,5-di-tert-butyl-4-hydroxyphenyl)propionate]. The antioxidant may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a light stabilizer, such as a sterically hindered amine, may be present in addition to the ultraviolet light stabilizer. Hindered amine light stabilizers that may be used include oligomeric hindered amine compounds that are N-methylated. For instance, hindered amine light stabilizer may comprise a high molecular weight hindered amine stabilizer. The light stabilizers, when present, may be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a lubricant, not including the tribological modifiers mentioned above, may be present. The lubricant may comprise a polymer wax composition. Further, in one embodiment, a polyethylene glycol polymer (processing aid) may be present in the composition. The polyethylene glycol, for instance, may have a molecular weight of from about 1000 to about 5000, such as from about 3000 to about 4000. In one embodiment, for instance, PEG-75 may be present. In another embodiment, a fatty acid amide such as ethylene bis(stearamide) may be present. Lubricants may generally be present in the polymer composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a compatibilizer, such as a phenoxy resin, may be present. Generally, the phenoxy resin may be present in the composition in an amount of at least about 0.01 wt. %, such as at least about 0.05 wt. %, such as at least about 0.075 wt. % and less than about 1 wt. %, such as less than about 0.75 wt. %, such as less than about 0.5 wt. %, wherein the weight is based on the total weight of the respective polymer composition.

In one embodiment, a colorant may be present. Colorants that may be used include any desired inorganic pigments, such as titanium dioxide, ultramarine blue, cobalt blue, and other organic pigments and dyes, such as phthalocyanines, anthraquinnones, and the like. Other colorants include carbon black or various other polymer-soluble dyes. The colorant may be present in the composition in an amount of at least about 0.01 wt. %, such as at least about 0.05 wt. %, such as at least about 0.1 wt. % and less than about 5 wt. %, such as less than about 2.5 wt. %, such as less than about 1 wt. %, wherein the weight is based on the total weight of the respective polymer composition.

In one embodiment, a coupling agent may be present. Coupling agents used include polyfunctional coupling agents, such as trifunctional or bifunctional agents. A suitable coupling agent is a polyisocyanate such as a diisocyanate. The coupling agent may provide a linkage between the polyoxymethylene polymer and the reinforcing fiber and/or sizing material coated on the reinforcing fiber. Generally, the coupling agent is present in an amount of at least about 0.1 wt. %, such as at least about 0.2 wt. % such as at least about 0.3 wt. % and less than about 5 wt. %, such as less than about 3 wt. %, such as less than about 1.5 wt. %. Alternatively, the composition may also be substantially free of any coupling agents such as less than about 0.2 wt. %, such as less than about 0.1 wt. %, such as less than about 0.05 wt. %, such as less than about 0.01 wt. %, such as about 0 wt. %.

In one embodiment, a reinforcing fiber may be present. The reinforcing fibers which may be used according to the present invention include mineral fibers, glass fibers, polymer fibers such as aramid fibers, metal fibers such as steel fibers, carbon fibers, or natural fibers. These fibers may be unmodified or modified, e.g. provided with a sizing or chemically treated, in order to improve adhesion to the polymer. Fiber diameters can vary depending upon the particular fiber used and whether the fiber is in either a chopped or a continuous form. The fibers, for instance, can have a diameter of from about 5 μm to about 100 μm, such as from about 5 μm to about 50 μm, such as from about 5 μm to about 15 μm. When present, the respective composition may contain reinforcing fibers in an amount of at least 1 wt. %, such as at least 5 wt. %, such as at least 7 wt. %, such as at least 10 wt. %, such as at least 15 wt. % and generally less than about 50 wt. %, such as less than about 45 wt. %, such as less than about 40 wt. %, such as less than about 30 wt. %, such as less than about 20 wt. %, wherein the weight is based on the total weight of the respective polyoxymethylene polymer composition. Alternatively, the polyoxymethylene polymer composition may also be substantially free of any reinforcing fibers, such that the composition contains fibers in an amount of less than about 0.1 wt. %, such as less than about 0.05 wt. %, such as less than about 0.01 wt. %, such as about 0 wt. %.

Polymer Articles

The compositions of the present disclosure can be compounded and formed into a polymer article using any technique known in the art. For instance, the respective composition can be intensively mixed to form a substantially homogeneous blend. The blend can be melt kneaded at an elevated temperature, such as a temperature that is higher than the melting point of the polymer utilized in the polymer composition but lower than the degradation temperature. Alternatively, the respective composition can be melted and mixed together in a conventional single or twin screw extruder. Preferably, the melt mixing is carried out at a temperature ranging from 100 to 280° C., such as from 120 to 260° C., such as from 140 to 240° C. or 180 to 220° C. However, such processing should be conducted for each respective composition at a desired temperature to minimize any polymer degradation.

After extrusion, the compositions may be formed into pellets. The pellets can be molded into polymer articles by techniques known in the art such as injection molding, thermoforming, blow molding, rotational molding and the like. According to the present disclosure, the polymer articles demonstrate excellent tribological behavior and mechanical properties. Consequently, the polymer articles can be used for several applications where low wear and excellent gliding properties are desired, Polymer articles include any moving articles or moldings that are in contact with another surface and may require high tribological requirements. For instance, polymer articles include articles for the automotive industry, especially housings, latches such as rotary latches, window winding systems, wiper systems, pulleys, sun roof systems, seat adjustments, levers, bushes, gears, gear boxes, claws, pivot housings, wiper arms, brackets or seat rail bearings, zippers, switches, cams, rollers or rolling guides, sliding elements or glides such as sliding plates, conveyor belt parts such as chain elements and links, castors, fasteners, levers, conveyor system wear strips and guard rails, medical equipment such as medical inhalers and injectors. An almost limitless variety of polymer articles may be formed from the polymer compositions of the present disclosure.

In one embodiment, the composition of the present disclosure is used to produce a first sliding member and a second sliding member. The first and second sliding members can both be made from a composition in accordance with the present disclosure. In particular, the first sliding member and the second sliding member can be made from a composition comprising a polyoxymethylene polymer in combination with an ultrahigh molecular weight silicone. The relative amounts of the components can be the same or can be different in each composition. Further, the polyoxymethylene polymer contained in the first sliding member can be the same or different than the polyoxymethylene polymer contained in the second sliding member. Similarly, the ultrahigh molecular weight silicone contained in the first sliding member can be the same or different than the ultrahigh molecular weight silicone contained in the second sliding member.

The first sliding member and the second sliding member can be contained in an apparatus and placed in operative association with each other such that the sliding members move relative to each other. For instance, in one embodiment, the first sliding member may be stationary while the second sliding member moves across the first sliding member. Alternatively, both sliding members may move while contacting each other.

The first sliding member and the second sliding member, in one embodiment, can be contained within or can otherwise be a part of an apparatus that has an operating environment over a wide temperature range and/or has an operating environment at relatively high temperatures and/or at relatively low temperatures. The sliding members made in accordance with the present disclosure, for instance, can exhibit a relatively low dynamic coefficient of friction over a broad temperature range and thus produce little to no noise during operation of the apparatus. In one embodiment, the apparatus can have an operating environment of from about −20° C. to about 100° C., such as from about 0° C. to about 60° C., The operating environment of the apparatus may include temperatures greater than 20° C., such as greater than 30° C., such as greater than 40° C., such as greater than 50° C., such as greater than 60° C. As used herein, the temperature of the operating environment of the apparatus can be based on internal temperatures that are produced or influenced by the apparatus or can refer to temperatures of the outside environment of the apparatus in which the apparatus operates.

In one particular embodiment, the apparatus comprises a coffeemaker 10 as shown in FIG. 1. Coffeemakers are designed to heat liquids very rapidly and produce a heated beverage. Consequently, the operating environment, especially the internal operating environment, of a coffeemaker can change from room temperature to high temperature relatively quickly. Coffeemakers, such as coffeemaker 10 as shown in FIG. 1, also have many moving parts. In accordance with the present disclosure, various internal and external parts of the coffeemaker can be made from the polymer composition of the present disclosure, especially two cooperating parts that slide relative to one another.

A coffee making apparatus typically comprises a water heating unit, a coffee supply unit, and a brewing assembly. For the production of a heated beverage, coffee is fed from the coffee supply unit and heated water from the water heating unit to the brewing assembly. Typical brewing assemblies comprise a brewing head, an upper closure element, a lower closure element, and at least one linear guide element.

Figure 2:
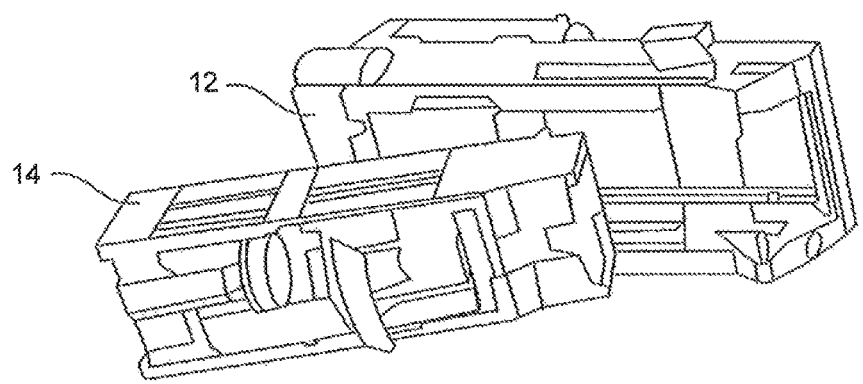
FIG. 2 is a perspective view of a first sliding member and a second sliding member that may be incorporated into the coffee maker apparatus of FIG. 1.

Referring to FIG. 2, the coffeemaker 10 can include a first sliding member 12 and a second sliding member 14. The first sliding member 12 and the second sliding member 14, in one embodiment, can be part of the brewing assembly or part of the coffee supply unit. For example, the sliding members 12 and 14 can be for receiving and loading coffee into a designated area, such as a capsule, for producing a coffee beverage. Because of close proximity to heated water, the sliding members 12 and 14 may experience an operating environment well above 30° C., such as greater than 40° C., such as greater than 50° C., such as even greater than 60° C. Sliding members made in accordance with the present disclosure can slide even at high temperatures while exhibiting a relatively low dynamic coefficient of friction that reduces or eliminates the generation of noise. By remaining silent during operation, consumers using the coffeemaker will have the impression that the coffeemaker is of high quality in addition to the coffeemaker having the capability of producing coffee while remaining very quiet.

In addition to coffeemakers, the sliding members of the present disclosure can be used in many different types of devices and products. For instance, the apparatus in other embodiments may comprise an automotive subassembly. The automotive subassembly may be a subassembly on the interior of the car or on the exterior of the car. The apparatus may also comprise another household appliance in addition to a coffeemaker. In still another embodiment, the apparatus may comprise a conveyor system where the first sliding member and the second sliding member remain in operative association during movement of the system.

Figure 3:
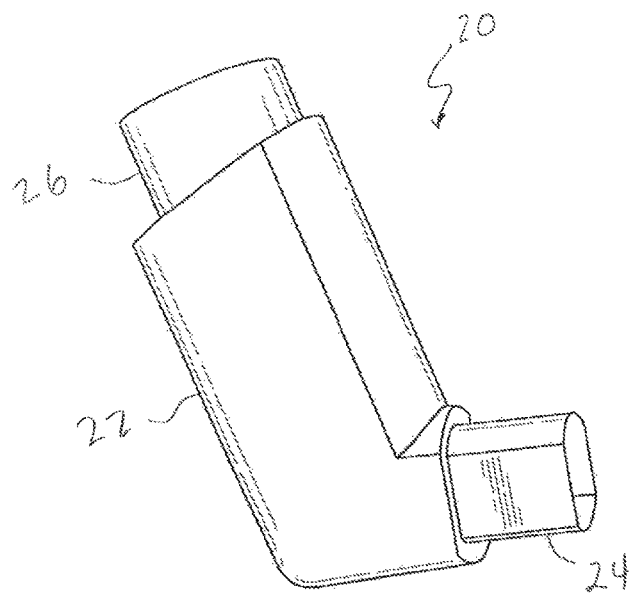
FIG. 3 is a perspective view of a medical inhaler made in accordance with the present disclosure.

In one embodiment, the sliding members of the present disclosure can be used to produce a medical product. For instance, referring to FIG. 3, an inhaler 20 is shown. The inhaler 20 includes a housing 22 attached to a mouthpiece 24. In operative association with the housing 22 is a plunger 26 for receiving a canister containing a composition to be inhaled. The composition may comprise a spray or a powder. The inhaler 20 can include a first sliding member in operative association with a second sliding member. For instance, in certain embodiments, the housing 22 may comprise the first sliding member while the plunger 26 may comprise the second sliding member. Alternatively, the first sliding member may comprise the housing 22 and the second sliding member may comprise the mouthpiece 24. In still another embodiment, an internal sliding member may be contained within the housing 22 that slides relative to the housing.

During use, the inhaler 20 administers metered doses of a medication, such as an asthma medication to a patient. The asthma medication may be suspended or dissolved in a propellant or may be contained in a powder. When a patient actuates the inhaler to breathe in the medication, a valve opens allowing the medication to exit the mouthpiece.

Figure 4:
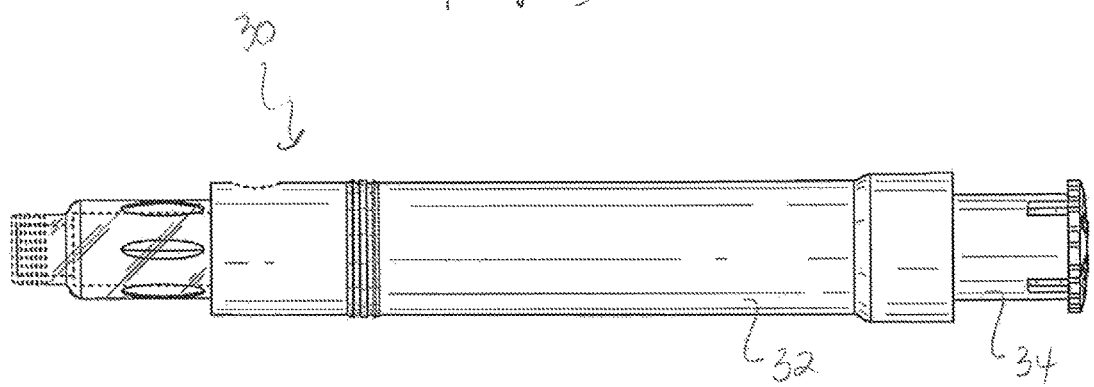
FIG. 4 is a side view of an injector that may be made in accordance with the present disclosure.

In another embodiment of the present disclosure, the first sliding member and the second sliding member are contained in a medical injector 30 as shown in FIG. 4. The medical injector 30 includes a housing 32 in operative association with a plunger 34. The housing 32 or first sliding member may slide relative to the plunger 34 or second sliding member. The medical injector 30 may be spring loaded. The medical injector 30 is for injecting a drug into a patient, typically into the thigh or the buttocks. The medical injector can be needleless or may contain a needle. When containing a needle, the needle tip is typically shielded within the housing prior to injection. Needleless injectors, on the other hand, can contain a cylinder of pressurized gas that propels a medication through the skin without the use of a needle.

Properties

Utilizing the polyoxymethylene polymer composition and polymer article produced therefrom according to the present disclosure provides compositions and articles with improved tribological properties. According to the present disclosure, the tribological properties are generally measured by the coefficient of friction.

In general, static friction is the friction between two or more surfaces that are not moving relative to each other (ie., both objects are stationary). In general, dynamic friction occurs when two objects are moving relative to each other (ie., at least one object is in motion or repeated back and forth motion). In addition, stick-slip is generally known as a phenomenon caused by continuous alternating between static and dynamic friction.

According to the present disclosure, the composition and polymer article may exhibit a static coefficient of friction against another surface, as determined according to VDA 230-206, of greater than about 0.01, such as greater than about 0.02, such as greater than about 0.03, such as greater than about 0.04, such as greater than about 0.05, such as greater than about 0.06 and generally less than about 0.2, such as less than about 0.18, such as less than about 0.15, such as less than about 0.12, such as less than about 0.1, such as less than about 0.9, such as less than about 0.8, such as less than about 0.7, such as less than about 0.6.

According to the present disclosure, the composition and polymer article may exhibit a dynamic coefficient of friction against another surface, as determined according to VDA 230-206, of greater than about 0.01, such as greater than about 0.02 and generally less than about 0.1, such as less than about 0.08, such as less than about 0.06, such as less than about 0.05, such as less than about 0.04.

In one embodiment, the above static coefficient of friction and dynamic coefficient of friction values and effect of sliding speed on the dynamic coefficient of friction are exhibited between the composition or polymer article and various counter-materials. For instance, the above values may be exhibited between the composition or polymer article and a polyester surface such as a polyethylene terephthalate surface. In another embodiment, the above values may be exhibited between the composition or polymer article and a polyacetal surface, a metal surface such as a steel surface, or a polyolefin surface such as a polypropylene surface or a polyethylene surface such as an ultra-high molecular weight polyethylene surface. As described above, in one embodiment, the countermaterial can also be made from the polymer composition of the present disclosure.

While the polyoxymethylene polymer composition and polymer articles produced therefrom of the present invention provide improved tribological properties, the compositions and articles may also exhibit improved mechanical properties. For instance, the modulus of elasticity, determined according to ISO Test No. 527, of the composition or polymer article may be greater than about 2000 MPa, such as greater than about 2200 MPa, such as greater than about 2400 MPa, such as greater than about 2500 MPa, such as greater than about 2600 MPa and generally less than about 10000 MPa, such as less than about 7500 MPa, such as less than about 5000 MPa, such as less than about 4000 MPa, such as less than about 3500 MPa, such as less than about 3000 MPa.

In one embodiment, the polymer article or molded polymer article may have topographical features that may provide surface characteristics and/or surface roughness on at least one surface of the article. For instance, the features may be ridges, valleys, protrusions, and the like on the surface of the article. These features may be present at the nanoscale or microscale level. Not to be limited by theory, the surface roughness may be produced during the molding of specific polymer articles. Surface roughness may also be produced depending on the particular additives present in the composition.

When in contact with a counter material, the surface roughness of the article may contribute to a reduced dynamic coefficient of friction when compared to the dynamic coefficient of friction of an article that exhibits a lesser degree of surface roughness. For instance, the dynamic coefficient of friction of an article exhibiting surface roughness may be less than the dynamic coefficient of friction of an article that is substantially free of surface roughness.

The surface roughness depth (Rz) may be measured according to DIN 4768 using a profilometer or roughness tester. The average surface roughness depth represents the mean from the individual depths of roughness of five individual lines. For instance, the measurements are made between the highest and lowest points on the surface averaged over five individual lengths.

In one embodiment, the article produced according to the present disclosure may have an average surface area roughness of greater than about 0.1 µm, such as greater than about 0.25 µm, such as greater than about 0.50 µm, such as greater than about 1 µm, such as greater than about 2.5 µm, such as greater than about 5 µm and less than about 30 µm, such as less than about 20 µm, such as less than about 15 µm, such as less than about 10 µm, such as less than about 5 µm, such as less than about 2.5 µm, such as less than about 1 µm.

The present disclosure may be better understood with reference to the following examples.

EXAMPLE NO. 1

The example of the invention is given below by way of illustration and not by way of limitation. The following experiments were conducted in order to show some of the benefits and advantages of the present invention.

Various polymer compositions comprising a polyoxymethylene polymer alone and with at least one tribological modifier were produced. In particular, the tribological modifiers included ultra-high molecular weight silicone, silicone oil, and polytetrafluoroethylene (PTFE) particles.

The components of each respective composition were mixed together and compounded using a ZSK 25MC (Werner & Pfleiderer, Germany) twin screw extruder (zone temperature 190° C., melt temperature about 210° C.). The screw configuration with kneading elements was chosen so that effective thorough mixing of the components took place. The compositions were extruded and pelletized. The pellets were dried for 8 hours at 120° C. and then injection molded.

The compositions/molds were tested for a variety of tribological and physical properties.

In this example, the tribological properties were determined for various compositions.

Stick-slip tests were conducted to determine the dynamic coefficient of friction. Stick-slip tests were conducted according to VDA 230-206. A ball-on-plate configuration was utilized with a load of 30 N, a sliding speed of 8 mm/s, and a test duration of 1000 cycles. The temperature was varied from −20° C. to 60° C. in order to determine the effect temperature has on the dynamic coefficient of friction.

The following polymer compositions were formulated and tested:

|  | Sample 1 | Sample 2 | Sample 3 | Sample 4 |
|---|---|---|---|---|
| POM copolymer (wt. %) | 100 | 98 | 97 | 82 |
| UHMW-Si (wt. %) | 0 | 0 | 3 | 0 |
| Silicone oil (wt. %) | 0 | 2 | 0 | 0 |
| PTFE (wt. %) | 0 | 0 | 0 | 18 |

For Sample Nos. 1, 2 and 4, the POM copolymer used was HF C9021 which has a melt volume flow rate of approximately 8.5 cm$^3$ per 10 mins. when tested according to ISO Test 1133 at a 190° C. and at a load of 2.16 kg. Sample No. 3 was formulated with HF C13031 polyoxymethylene copolymer which has a melt volume flow rate of 12 cm$^3$ per 10 mins.

The above compositions were formulated into test specimens which comprised sliding pairs. The sliding pairs were then subjected to the stick-slip test at a temperature of −20° C., at a temperature of 23° C., and at a temperature of 60° C. The compositions were tested against sample No. 1 and against themselves in determining the dynamic coefficient of friction.

In addition to determining the dynamic coefficient of friction, a noise rating test was conducted. The noise rating test was conducted according to Test VDA 230-206.

The following results were obtained:

| Sliding Pairs | Test Temperature = −20° C. | | Test Temperature = 23° C. | | Test Temperature = 60° C. | |
|---|---|---|---|---|---|---|
|  | Dynamic CoF | Noise Rating | Dynamic CoF | Noise Rating | Dynamic CoF | Noise Rating |
| Sample 1 v. Sample 1 | 0.286 | 10 | 0.342 | 10 | 0.341 | 10 |
| Sample 1 v. Sample 3 | 0.09 | 3 | 0.034 | 3 | 0.078 | 9 |
| Sample 1 v. Sample 4 | 0.154 | 2 | 0.098 | 1 | 0.09 | 6 |
| Sample 3 v. Sample 3 | 0.069 | 3 | 0.034 | 3 | 0.024 | 3 |
| Sample 4 v. Sample 4 | 0.139 | 2 | 0.091 | 4 | 0.082 | 4 |
| Sample 2 v. Sample 2 | — | — | 0.048 | 6 | 0.225 | 10 |

As shown above, Sample No. 3 where the polyoxymethylene polymer was combined with an ultrahigh molecular weight silicone displayed no noise risk over the entire temperature range of from −20° C. to 60° C. when tested against itself. This result is unexpected and surprising especially in relation to the other samples.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A low friction assembly comprising:
a first sliding member in operative association with a second sliding member, the first sliding member and the second sliding member being configured to remain in contact and move relative to each other, each sliding member comprising a molded polymeric article, the first sliding member being made from a first polymer composition comprising a polyoxymethylene polymer combined with an ultrahigh molecular weight silicone, the second sliding member being made from a second polymer composition comprising a polyoxymethylene polymer combined with an ultrahigh molecular weight silicone, and wherein the first polymer composition and the second polymer composition are free of silicone oils, the ultrahigh molecular weight silicone being present in the first polymer composition and the second polymer composition such that when the polymer compositions are tested against each other, the compositions exhibit a dynamic coefficient of friction of less than about 0.06 when tested at a temperature of 60° C. and at a sliding speed of 8 mm/s.

2. A low friction assembly as defined in claim 1, wherein the first polymer composition and the second polymer composition have a noise rating of 3 or less when tested against each other within a temperature range from −20° C. to 60° C.

3. A low friction assembly as defined in claim 1, wherein the first polymer composition is the same as the second polymer composition.

4. A low friction assembly as defined in claim 1, wherein the ultrahigh molecular weight silicone contained in the first polymer composition and contained in the second polymer composition comprises a dialkylpolysiloxane, an alkylarylsiloxane, a diarylsiloxane and/or a polysilsesquioxane.

5. A low friction assembly as defined in claim 1, wherein at least the first sliding member exhibits a wear track width of less than 0.5 mm when tested against a countermaterial at 60° C. at a force of 30 N and at a velocity of 8 mm/s after 1,000 cycles, the countermaterial comprising the polyoxymethylene polymer contained in the sliding member.

6. A low friction assembly as defined in claim 1, wherein the first polymer composition and the second polymer composition contain an ultrahigh molecular weight silicone in different amounts.

7. A low friction assembly as defined in claim 1, wherein the first polymer composition and the second polymer composition contain an ultrahigh molecular weight silicone in the same amounts.

8. A low friction assembly as defined in claim 1, wherein the first polymer composition and the second polymer composition contain the ultrahigh molecular weight silicone in an amount from about 0.5% to about 10% by weight.

9. A low friction assembly as defined in claim 1, wherein the ultrahigh molecular weight silicone contained in the first polymer composition and contained in the second polymer composition have a kinematic viscosity of greater than about 100,000 $mm^2s^{-1}$.

10. A low friction assembly as defined in claim 1, wherein the first sliding member and the second sliding member are free of any silicone oils having a molecular weight of less than about 75,000 g/mol.

11. A low friction assembly as defined in claim 1, wherein the ultrahigh molecular weight silicone contained in the first composition comprises an ultrahigh molecular weight polydimethylsiloxane.

12. A low friction assembly as defined in claim 1, wherein the polyoxymethylene polymer contained in the first composition and the polyoxymethylene polymer contained in the second composition both comprise polyoxymethylene copolymers having a melt index of from about 0.5 g/10 min to about 50 g/10 min when measured at 190° C. and at a load of 2.16 kg.

13. A low friction assembly as defined in claim 1, wherein the low friction assembly comprises a medical inhaler or injector.

* * * * *